(12) United States Patent
Boukhris

(10) Patent No.: US 6,235,035 B1
(45) Date of Patent: May 22, 2001

(54) BONE RECOVERING SURGICAL DRILL COMPRISING A STOP HAVING A COLORED MARK

(75) Inventor: Gilles Boukhris, Paris (FR)

(73) Assignee: Societe Implants Diffusion, Paris (FR)

( * ) Notice: Subject to any disclaimer, the term of this patent is extended or adjusted under 35 U.S.C. 154(b) by 0 days.

(21) Appl. No.: 09/403,294
(22) PCT Filed: Apr. 15, 1998
(86) PCT No.: PCT/FR98/00760
  § 371 Date: Mar. 20, 2000
  § 102(e) Date: Mar. 20, 2000
(87) PCT Pub. No.: WO98/48708
  PCT Pub. Date: Nov. 5, 1998

(30) Foreign Application Priority Data

Apr. 30, 1997 (FR) .................................................. 97 05387

(51) Int. Cl.⁷ ...................................................... A61B 17/00
(52) U.S. Cl. ................................ 606/80; 606/72; 606/73; 433/165
(58) Field of Search .................................. 606/80, 79, 81, 606/86, 96, 97, 98, 72, 73, 61; 408/225, 224, 16; 433/165, 102, 72, 75, 141

(56) References Cited

U.S. PATENT DOCUMENTS

| | | | |
|---|---|---|---|
| 4,710,075 | * 12/1987 | Davison | 408/202 |
| 5,573,537 | * 11/1996 | Rogozinski | 606/80 |
| 5,741,267 | * 4/1998 | Jorneus et al. | 606/80 |
| 5,941,706 | * 8/1999 | Ura | 433/165 |

* cited by examiner

Primary Examiner—Pedro Philogene
(74) Attorney, Agent, or Firm—Hodgson Russ LLP

(57) ABSTRACT

The invention relates to a bone recovering surgical drill comprising an active portion (A) and a non-active portion (E), having between the active and non-active portions one or more circular grooves (f) the depth and width of which are sufficient for recovering the drilled bone residues, as well as a stop with a diameter larger than that of the active portion (A), the purpose of which is to limit the penetration of the drill. The stop is a fixed stop with a coloured mark (d) on said stop.

3 Claims, 2 Drawing Sheets

BONE RECOVERING SURGICAL DRILL COMPRISING A STOP HAVING A COLORED MARK

BACKGROUND OF THE INVENTION

Figure 1:
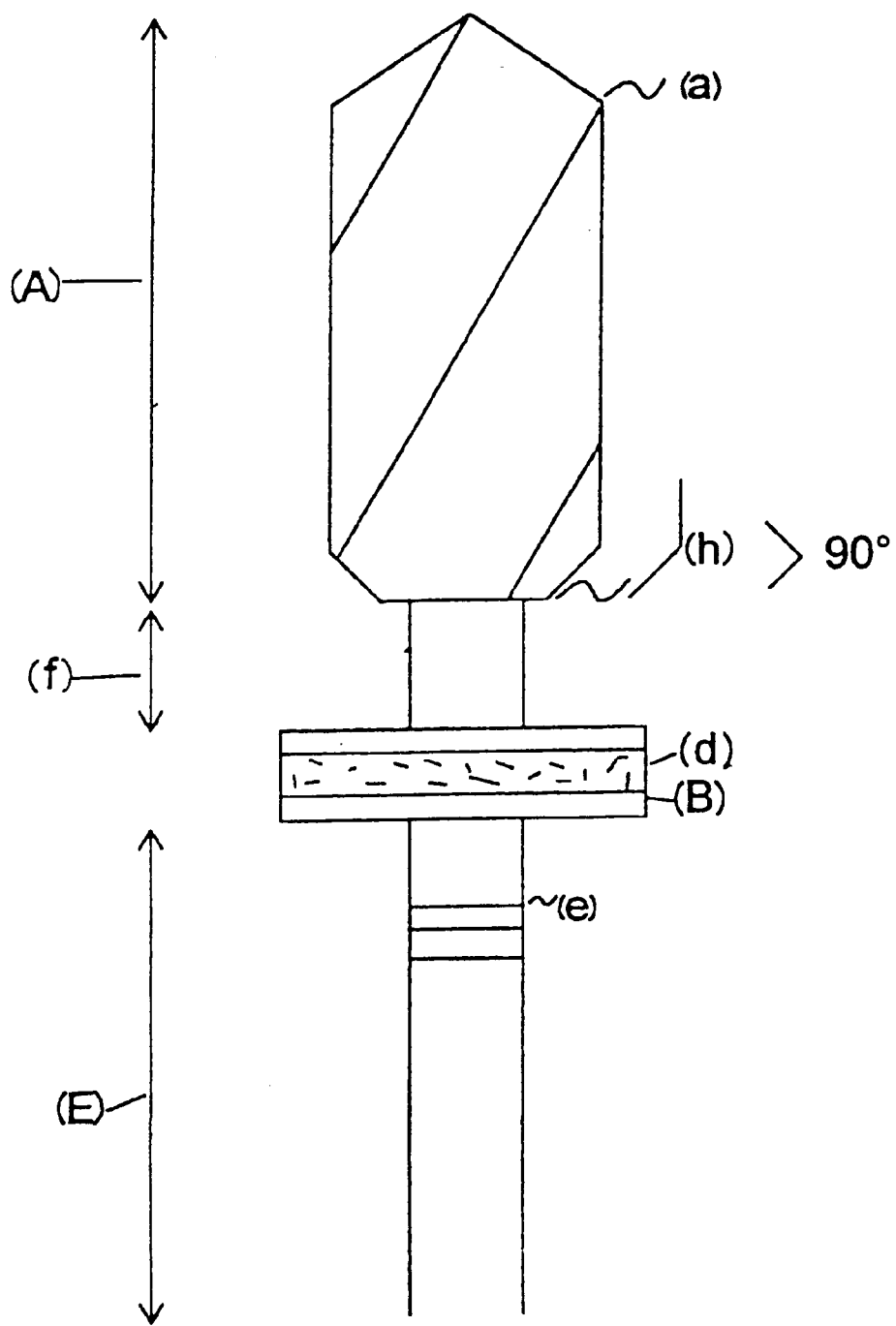

The present invention relates to a bone recovering surgical drill, with a stop to limit its penetration, having one or more deep circular grooves between the active portion of the drill and the stop to retain the drilled bone residues, according to the preamble of claim 1.

SUMMARY OF THE INVENTION

Such a drill is known from document U.S. Pat. No. 4,710,075. The present invention provides a drill additionally comprising the characteristics contained in the second part of claim 1. In the dependent claims, particular embodiments are indicated.

Said bone can, in a second stage, be recovered for the purposes of bone grafts.

BRIEF DESCRIPTION OF THE DRAWING FIGURES

Figure 2:
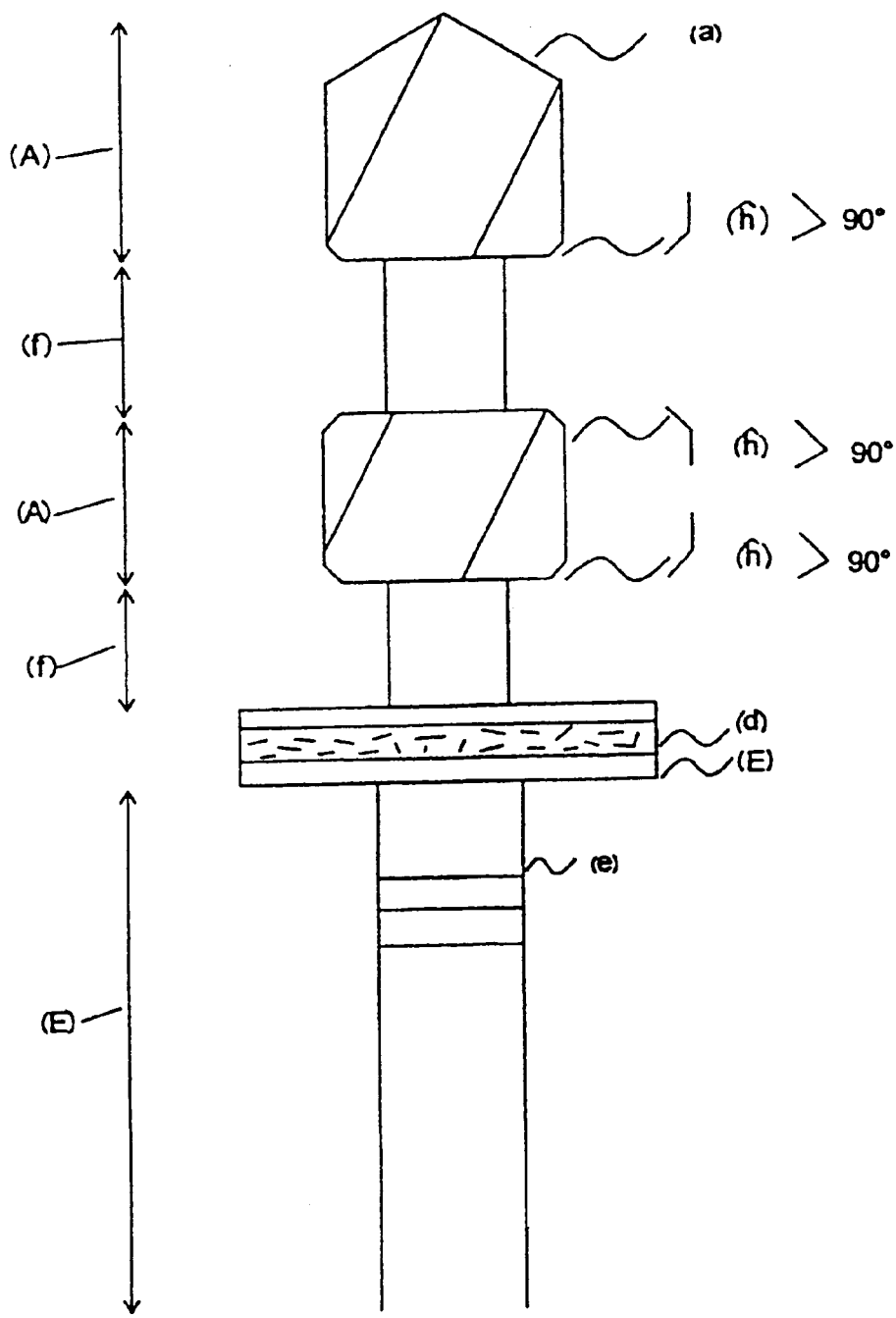

FIG. 1 is a fragmentary elevational view illustrating the bone recovering surgical drill according to the present invention; and FIG. 2 is a fragmentary elevational view further illustrating the bone recovering surgical drill according to the present invention.

DETAILED DESCRIPTION OF THE INVENTION

The bone recovering surgical drill has, or can have, five specific features:

a) a fixed stop (B) having a diameter which is larger than that of the active portion, serving to limit the penetration of the drill, and serving as a cover for the bone recovery area;

b) a coloured mark (d) extending over the stop to enable the distance between the tip of the drill and the stop to be determined;

c) a mark (e) on the smooth, non-active portion (E) of the drill to enable the diameter of the drill to be determined;

d) one or more circular spaces (f) between the tip of the drill and the stop, the role of which is to recover the drilled bone residues; this/these space(s) can be 1 to several mm wide, and said circular groove(s) must have a depth of 1 to several mm, depending on the strength of the drill; and e) the active portion (A) ends with an angle (h) of more than 90° to facilitate the withdrawal of the spinning instrument.

What is claimed is:

1. Bone recovering surgical drill comprising an active portion (A) and a non-active portion (E), having between the active and non-active portions one or more circular grooves wherein the drill comprises at least one groove (f), the depth and width of which are sufficient for recovering the drilled bone residues, as well as a stop with a diameter larger than that of the active portion (A), the purpose of which is to limit the penetration of the drill, the stop being a fixed stop with a coloured mark (d).

2. Bone recovering surgical drill according to claim 1, characterised in that the circular groove or grooves (f) is/are 1 to several mm deep and 1 to several mm wide.

3. Bone recovering surgical drill according to claim 1, characterised in that the drill has, on its non-active portion (E) a mark (e) indicating the diameter of the drill.

* * * * *